(12) United States Patent
Aratake et al.

(10) Patent No.: US 9,683,228 B2
(45) Date of Patent: Jun. 20, 2017

(54) METHOD FOR STABILIZING CHOLESTEROL OXIDASE

(71) Applicant: KYOWA MEDEX CO., LTD., Chuo-ku, Tokyo (JP)

(72) Inventors: Tomoko Aratake, Sunto-gun (JP); Kenta Kinjo, Sunto-gun (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 0 days.

(21) Appl. No.: 14/391,512

(22) PCT Filed: Apr. 18, 2013

(86) PCT No.: PCT/JP2013/061529
§ 371 (c)(1),
(2) Date: Oct. 9, 2014

(87) PCT Pub. No.: WO2013/161676
PCT Pub. Date: Oct. 31, 2013

(65) Prior Publication Data
US 2015/0104847 A1    Apr. 16, 2015

(30) Foreign Application Priority Data

Apr. 27, 2012  (JP) ................................. 2012-103257
May 25, 2012  (JP) ................................. 2012-119583

(51) Int. Cl.
*C12N 9/96*     (2006.01)
*C12N 9/04*     (2006.01)

(52) U.S. Cl.
CPC ............. *C12N 9/96* (2013.01); *C12N 9/0006* (2013.01); *C12Y 101/03006* (2013.01)

(58) Field of Classification Search
CPC ...................................................... C12N 9/96
See application file for complete search history.

(56) References Cited

U.S. PATENT DOCUMENTS

| | | |
|---|---|---|
| 4,366,249 A | 12/1982 | Thum et al. |
| 5,047,327 A | 9/1991 | Caris et al. |
| 6,818,414 B1 | 11/2004 | Nakamura et al. |

FOREIGN PATENT DOCUMENTS

| | | |
|---|---|---|
| DE | 27 55 799 | 8/1978 |
| EP | 0 080 304 | 6/1983 |
| JP | 52-143285 | 11/1977 |
| JP | 06-062846 | 3/1994 |
| JP | 08-187095 | 7/1996 |
| JP | 2002-233363 | 8/2002 |
| JP | 2005-114368 | 4/2005 |
| JP | 2010-172346 | 8/2010 |

OTHER PUBLICATIONS

Whitehouse et al. JBC, 1961, 236:68-72.*
Vidal et al. Analytica Chimica Acta, 1999, 385:213-222.*

* cited by examiner

*Primary Examiner* — Bin Shen
(74) *Attorney, Agent, or Firm* — Fitzpatrick, Cella, Harper & Scinto

(57) ABSTRACT

The present invention provides a method for stabilizing a cholesterol oxidase, a method for preserving a cholesterol oxidase, and a stabilized composition of cholesterol oxidase. A method for stabilizing a cholesterol oxidase and a method for preserving a cholesterol oxidase which comprises allowing the cholesterol oxidase to coexist with an α-keto acid in an aqueous medium, and, a stabilized composition of cholesterol oxidase which comprises the cholesterol oxidase being allowed to coexist with an α-keto acid in an aqueous medium. The method for stabilizing a cholesterol oxidase, the method for preserving a cholesterol oxidase, and a stabilized composition of cholesterol oxidase according to the present invention are useful for clinical diagnosis such as metabolic syndrome.

2 Claims, No Drawings

METHOD FOR STABILIZING CHOLESTEROL OXIDASE

This application is a national phase of PCT Application No. PCT/JP2013/061529 filed Apr. 18, 2013, which in turn claims benefit of Japanese Application Nos. 2012-103257 filed Apr. 27, 2012 and 2012-119583 filed May 25, 2012.

TECHNICAL FIELD

The present invention relates to a method for stabilizing a cholesterol oxidase, a method for preserving a cholesterol oxidase, and a stabilized composition of cholesterol oxidase.

BACKGROUND ART

A cholesterol oxidase is an oxidoreductase which acts on cholesterol and oxygen molecule as a substrate. Measurement of cholesterol using a cholesterol oxidase is often carried out in clinical tests. A method for measuring cholesterol in a specimen by a colorimetric method or the like is used in clinical tests. In such a colorimetric method, the cholesterol oxidase acts on cholesterol in a specimen to form hydrogen peroxide, the hydrogen peroxide formed is reacted with an oxidative-coloring chromogen in the presence of a peroxidase to convert the chromogen to a dye, and the absorbance of the dye formed is measured.

A cholesterol oxidase used for measuring cholesterol is unstable. The problem of the cholesterol oxidases is that the cholesterol oxidase is deactivated during preservation of a reagent for measuring which contains the cholesterol oxidase to give a reduced performance of the reagent for measuring.

A method for stabilizing a cholesterol oxidase, wherein alkali metal chloride and/or alkaline earth metal chloride are added to a solution containing the cholesterol oxidase (see patent document 1), a method for stabilizing a cholesterol oxidase in solution, wherein the cholesterol oxidase is chemically bound to a water-soluble carrier selected from bovine serum albumin, dextran, and polyethylene glycol (see patent document 2), a method for stabilizing a cholesterol oxidase by adding of bovine serum albumin and lysine to a solution containing the cholesterol oxidase (see patent document 3), a method for stabilizing a cholesterol oxidase in a dried state by allowing the cholesterol oxidase to coexist with protein decomposition products (see patent document 4), and the like are known for this problem.

PRIOR ART DOCUMENTS

Patent Documents

Patent Document 1: Japanese unexamined Patent Application Publication No. 52-143285
Patent Document 2: Japanese unexamined Patent Application Publication No. 6-062846
Patent Document 3: Japanese unexamined Patent Application Publication No. 8-187095
Patent Document 4: Japanese unexamined Patent Application Publication No. 2005-114368

SUMMARY OF THE INVENTION

Problems to be Solved by the Invention

An object of the present invention is to provide a method for stabilizing a cholesterol oxidase suitable for long-term preservation, a method for preserving a cholesterol oxidase, and a stabilized composition of cholesterol oxidase.

Means to Solve the Problems

The present inventors have found that, as a result of intensive studies to solve the problem, coexistence of a cholesterol oxidase with an α-keto acid or a salt thereof in an aqueous medium enables to keep the cholesterol oxidase stable, thereby completing the present invention. That is, the present invention relates to the following [1] to [6].
[1] A method for stabilizing a cholesterol oxidase which comprises allowing the cholesterol oxidase to coexist with an α-keto acid or a salt thereof in an aqueous medium.
[2] The method for stabilizing a cholesterol oxidase according to [1], wherein the α-keto acid is an α-keto acid selected from the group of consisting of pyruvic acid, α-ketoglutaric acid, and oxaloacetic acid.
[3] A method for preserving a cholesterol oxidase which comprises allowing the cholesterol oxidase to coexist with an α-keto acid or a salt thereof in an aqueous medium.
[4] The method for preserving a cholesterol oxidase according to [3], wherein the α-keto acid is an α-keto acid selected from the group of consisting of pyruvic acid, α-ketoglutaric acid, and oxaloacetic acid.
[5] A stabilized composition of cholesterol oxidase which comprises the cholesterol oxidase being allowed to coexist with an α-keto acid or a salt thereof in an aqueous medium.
[6] The stabilized composition of cholesterol oxidase according to [5], wherein the α-keto acid is an α-keto acid selected from the group of consisting of pyruvic acid, α-ketoglutaric acid, and oxaloacetic acid.

Effect of the Invention

The present invention provides a method for stabilizing a cholesterol oxidase suitable for long-term preservation, a method for preserving a cholesterol oxidase, and a stabilized composition of cholesterol oxidase.

MODE OF CARRYING OUT THE INVENTION

A method for stabilizing a cholesterol oxidase according to the present invention is a method which comprises allowing the cholesterol oxidase to coexist with an α-keto acid or a salt thereof in an aqueous medium.

A method for preserving a cholesterol oxidase according to the present invention is a method which comprises allowing the cholesterol oxidase to coexist with an α-keto acid or a salt thereof in an aqueous medium.

A stabilized composition of cholesterol oxidase according to the present invention is a composition which comprises the cholesterol oxidase being allowed to coexist with an α-keto acid or a salt thereof in an aqueous medium.

"Stabilization" in the present invention means that the enzyme activity of a cholesterol oxidase is maintained even if the cholesterol oxidase is preserved for a long period, and means that, specifically, after an aqueous solution of a cholesterol oxidase is preserved at 5° C. for 2 weeks, the activity of the cholesterol oxidase after preservation at 5° C. for 2 weeks is 75% or more of the activity of the cholesterol oxidase immediately after preparation of the aqueous solution of the cholesterol oxidase. The activity of a cholesterol oxidase can be measured by the following method, for example.

A reagent for evaluating a cholesterol oxidase activity comprising cholesterol and a reagent for detection is prepared. As the reagent for detection, a reagent comprising a peroxidase and an oxidative-coloring chromogen described below can be used, for example. The reagent (y μL) for evaluating the cholesterol oxidase activity is added to a specimen A (xμL) and the reaction is carried out at 37° C. for 5 minutes, and the absorbance of the reaction solution 5 minutes after the reaction, $E1_A$, is measured. The reaction is further carried out at 37° C. for 5 minutes, the absorbance of the reaction solution 10 minutes after the reaction, $E2_A$, is measured, and the difference in the absorbances, $\Delta E'_A$ is calculated by subtracting $E1_A$ from $E2_A$. The absorbance of the reaction solution after the reaction at 37° C. for 5 minutes, $E1_0$, is measured by the same method except that distilled water is used as a specimen instead of the specimen A. The reaction is further carried out at 37° C. for 5 minutes, and the absorbance of the reaction solution 10 minutes after the reaction, $E2_0$, is measured, and the difference in the absorbances, $\Delta E_0$ is calculated by subtracting $E1_0$ from $E2_0$. $\Delta E_0$ is subtracted from $\Delta E'_A$ to thereby provide the difference in the absorbances, $\Delta E_A$ for the specimen A. This difference in the absorbances, $\Delta E_A$ is used to calculate the activity of the cholesterol oxidase. In case a combination of 4-aminoantipyrine (4-AA) and N-ethyl-N-(3-methylphenyl)-N'-succinylethylenediamine (EMSE) is used as an oxidative-coloring chromogen, the activity of the cholesterol oxidase is calculated from the following expression (I):

[Expression 1]

$$\text{Cholesterol oxidase activity (U/mL)} = \Delta E_A / 16.9 * (x+y)/x \quad (I)$$

As can be seen from the expression (I) described above, the activity of the cholesterol oxidase is proportional to $\Delta E_A$, and thus $\Delta E_A$ can be used as an indicator of the activity of the cholesterol oxidase.

Stabilization of the cholesterol oxidase can be evaluated, for example, by the following method. As for a specimen A prepared by adding a cholesterol oxidase and α-keto acid to a buffer solution as a specimen containing the cholesterol oxidase, a specimen $A_{(immediately\ after\ preparation)}$ immediately after preparation and a specimen $A_{(after\ preservation)}$ obtained after preservation of the specimen $A_{(immediately\ after\ preparation)}$ at 5° C. for 2 weeks are prepared. Additionally, as for a specimen a which is prepared by adding only the cholesterol oxidase to a buffer solution and contains no α-keto acid, a specimen $a_{(immediately\ after\ preparation)}$ immediately after preparation and a specimen $a_{(after\ preservation)}$ obtained after preservation of the specimen $a_{(immediately\ after\ preparation)}$ at 5° C. for 2 weeks are prepared. Reaction of the specimen $A_{(immediately\ after\ preparation)}$ with a reagent for evaluating the cholesterol oxidase activity is carried out at 37° C. for 5 minutes using the specimen $A_{(immediately\ after\ preparation)}$ as a specimen, and then, the absorbance of the reaction solution, $E1_{A(immediately\ after\ preparation)}$, is measured. The reaction is further carried out at 37° C. for 5 minutes, and the absorbance of the reaction solution 10 minutes after the reaction, $E2_{A(immediately\ after\ preparation)}$, is measured. The difference in the absorbances, $\Delta E'_{A(immediately\ after\ preparation)}$ is calculated by subtracting $E1_{A(immediately\ after\ preparation)}$ from $E2_{A(immediately\ after\ preparation)}$. The absorbance of the reaction solution after the reaction at 37° C. for 5 minutes, $E1_0$, is measured by the same method except that distilled water is used as a specimen instead of the specimen $A_{(immediately\ after\ preparation)}$. The reaction is further carried out at 37° C. for 5 minutes, and the absorbance of the reaction solution 10 minutes after the reaction, $E2_0$, is measured. $E1_0$ is subtracted from $E2_0$ to thereby calculate the difference in the absorbances, $\Delta E_0$. $\Delta E_0$ is subtracted from $\Delta E'_{A(immediately\ after\ preparation)}$ to thereby provide the difference in the absorbances, $\Delta E_{A(immediately\ after\ preparation)}$ for the specimen $A_{(immediately\ after\ preparation)}$.

The difference in the absorbances, $\Delta E_{A(after\ preservation)}$ for the specimen $A_{(after\ preservation)}$ is calculated by the same method as described above except that the specimen $A_{(after\ preservation)}$ is used as a specimen instead of the specimen $A_{(immediately\ after\ preparation)}$. Similarly, the difference in the absorbances, $\Delta E_{a(immediately\ after\ preparation)}$ for the specimen $a_{(immediately\ after\ preparation)}$ is calculated using the specimen $a_{(immediately\ after\ preparation)}$ as a specimen instead of the specimen $A_{(immediately\ after\ preparation)}$, and the difference in the absorbances, $\Delta E_{a(after\ preservation)}$ for the specimen $a_{(after\ preservation)}$ is calculated using the specimen $a_{(after\ preservation)}$ as a specimen instead of the specimen $A_{(immediately\ after\ preparation)}$. The residual ratio of the cholesterol oxidase in the specimen A is calculated from the following expression (II):

[Expression 2]

$$\text{Residual ratio (\%)} = \Delta E_{A(after\ preservation)} / \Delta E_{A(immediately\ after\ preparation)} * 100 \quad (II)$$

Similarly, the residual ratio of the cholesterol oxidase in the specimen a is calculated from the following expression (III):

[Expression 3]

$$\text{Residual ratio (\%)} = \Delta E_{a(after\ preservation)} / \Delta E_{a(immediately\ after\ preparation)} * 100 \quad (III)$$

In case the residual ratio of the cholesterol oxidase in the specimen A calculated from the expression (II) described above is 75% or more and higher than the residual ratio of the cholesterol oxidase in the specimen a calculated from the expression (III) described above, it can be evaluated that the cholesterol oxidase has been stabilized with the α-keto acid.

The cholesterol oxidase in the present invention is an enzyme classified in EC1.1.3.6 and catalyzing the following reaction:

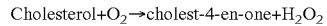

$$\text{Cholesterol} + O_2 \rightarrow \text{cholest-4-en-one} + H_2O_2$$

Examples of the cholesterol oxidase catalyzing the reaction described above include: a cholesterol oxidase derived from animals, plants or microorganisms; and a cholesterol oxidases manufactured by a genetic engineering method. There can be used commercially available products such as a cholesterol oxidase (CHODI; manufactured by KIKKOMAN CORPORATION), a cholesterol oxidase (CHOPEWL; manufactured by KIKKOMAN CORPORATION), a cholesterol oxidase (CHO-CE; manufactured by KIKKOMAN CORPORATION), and a cholesterol oxidase (COO-321; manufactured by TOYOBO CO., LTD.).

The aqueous medium in the present invention is not particularly limited as long as it is an aqueous medium which can keep the cholesterol oxidase stable. Examples of the aqueous medium include a deionized water, a distilled water, and a buffer solution, and is preferred a buffer solution. The concentration of the cholesterol oxidase in an aqueous medium in the present invention is usually from 0.01 to 300 U/mL. A buffer having a buffering capacity in the pH region where the cholesterol oxidase can be kept stable is preferred as a buffer solution. Examples include a phosphate buffer solution, a borate buffer solution, and a Good's buffer solution. Examples of the Good's buffer used in the Good's buffer solution include 2-morpholinoethanesulfonic acid (MES), tris(hydroxymethyl)aminomethane (Tris), bis (2-hydroxyethyl)iminotris(hydroxymethyl)methane (Bis-Tris), N-(2-acetamide)iminodiacetic acid (ADA), piperazine-N,N'-bis(2-ethanesulfonic acid) (PIPES), N-(2-acetamide)-2-aminoethanesulfonic acid (ACES), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), piperazine-N,N'-bis(2-hydroxypropanesulfonic acid) (POPSO), N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), and N-cyclohexyl-3-aminopropanesulfonic acid (CAPS).

In the present invention, the cholesterol oxidase is usually preserved in an aqueous medium having a pH from 5 to 9 and preferably preserved in an aqueous medium having a pH from 6 to 8.

The $\alpha$-keto acid in the present invention is not particularly limited as long as it is an $\alpha$-keto acid which can stabilize the cholesterol oxidase, and examples include pyruvic acid, $\alpha$-ketoglutaric acid, and oxaloacetic acid. In the present invention, the $\alpha$-keto acid may be a salt, and examples of the salt include a lithium salt, a sodium salt, a potassium salt, an ammonium salt, a calcium salt, and a magnesium salt.

The concentration of the $\alpha$-keto acid in an aqueous medium in the present invention is not particularly limited as long as it is a concentration which can stabilize the cholesterol oxidase and is usually from 0.05 to 40 mmol/L.

A method for preserving a cholesterol oxidase according to the present invention is a method which comprises allowing the cholesterol oxidase to coexist with an $\alpha$-keto acid or a salt thereof in an aqueous medium. Examples of the cholesterol oxidase and the concentration thereof and the $\alpha$-keto acid and the concentration thereof used in the method for preserving a cholesterol oxidase according to the present invention are the same as those used in the method for stabilizing a cholesterol oxidase mentioned above. The preservation period in the method for preserving a cholesterol oxidase according to the present invention is not particularly limited as long as it is a period during which the cholesterol oxidase is stably preserved, and is usually from 1 to 2 years. Moreover, the preservation temperature in the method for preserving a cholesterol oxidase according to the present invention is not particularly limited as long as it is a temperature at which the cholesterol oxidase is stably preserved, and is usually from −5 to 45° C., preferably from 0 to 30° C., and particularly preferably from 2 to 10° C.

In the method for preserving a cholesterol oxidase according to the present invention, a surfactant, a preservative, a protein, and the like as well as an $\alpha$-keto acid and a salt thereof can coexist with the cholesterol oxidase. Examples of the surfactant include a nonionic surfactant, a cationic surfactant, an anionic surfactant, and an amphoteric surfactant. Examples of the preservative include an azide and a chelator. Examples of the azide include sodium azide. Examples of the chelator include ethylenediaminetetraacetic acid (EDTA) and a salt thereof. Examples of the salt include a sodium salt and a potassium salt. Examples of the protein include albumin, and examples of albumin include bovine serum albumin (BSA).

A stabilized composition of cholesterol oxidase according to the present invention may include components usually included in a reagent and a kit used in a method for measuring a component to be measured based on a hydrogen peroxide measuring system, in addition to a cholesterol oxidase and an $\alpha$-keto acid or a salt thereof. Examples of the component to be measured include total cholesterol (TC), cholesterol in high-density lipoprotein (HDL-C), cholesterol in intermediate-density lipoprotein (IDL-C), cholesterol in low-density lipoprotein (LDL-C), cholesterol in very-low-density lipoprotein (VLDL-C), cholesterol in remnant-like lipoprotein (RLP-C), cholesterol in small dense low-density lipoprotein (sdLDL-C), cholesterol in HDL subfractions (HDL2-C, HDL3-C), and free cholesterol (FC).

The reagent and kit used in the method for measuring cholesterol (TC, HDL-C, LDL-C, IDL-C, VLDL-C, RLP-C, sdLDL-C, HDL2-C, HDL3-C, and FC) include, for example, a cholesterol esterase, a peroxidase, and an oxidative-coloring chromogen in addition to an cholesterol oxidase.

Examples of the oxidative-coloring chromogen include a leuco chromogen and an oxidative-coupling chromogen.

The leuco chromogen has a function of reacting with hydrogen peroxide in the presence of a peroxidase to thereby in itself form a dye. Examples of the leuco chromogen include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino) diphenylamine sodium salt (DA-64), 10-N-(carboxymethylaminocarbonyl)-3,7-bis(dimethylamino)-10H-phenothiazine sodium salt (DA-67), 4,4'-bis(dimethylamino) diphenylamine, and bis[3-bis(4-chlorophenyl)methyl-4-dimethylaminophenyl]amine (BCMA).

The oxidative coupling coloring chromogen has a function of reacting with hydrogen peroxide in the presence of a peroxidase to thereby form a dye. In this reaction to form a dye, a combination of a pair of oxidative coupling-coloring chromogens is used. Examples of the combination of the pair of oxidative coupling coloring chromogens include a combination of a coupler and an aniline and combinations of a coupler and a phenol.

Examples of the coupler include 4-aminoantipyrine (4-AA) and 3-methyl-2-benzothiazolinone hydrazine.

Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

The stabilized composition of cholesterol oxidase according to the present invention may comprise the surfactant, preservative, and protein mentioned above.

Hereinbelow, the present invention is described more specifically according to Examples, but these Examples are not intended to limit the scope of the present invention in any way. It is to be noted that reagents and enzymes from the following manufacturers were used in Examples, Comparative Examples, and Test Examples.

MOPS (manufactured by DOJINDO LABORATORIES), EMSE (manufactured by Daito Chemix Corporation), 4-AA (manufactured by ACTEC, Inc.), BioAce (manufactured by KI Chemical Industry Co., Ltd.), PGM-50 (polyoxyethylene octylphenyl ether; manufactured by Wako Pure Chemical Industries, Ltd.), sodium cholate (manufactured by NACALAI TESQUE, INC.), cholesterol (manufactured by JUNSEI CHEMICAL CO., LTD.), 2-propanol (manufactured by Wako Pure Chemical Industries, Ltd.), Triton X-100 (manufactured by Sigma Chemical Company), sodium pyruvate (manufactured by KANTO CHEMICAL CO., INC.), α-ketoglutaric acid disodium (manufactured by MP Biomedicals, LLC.), oxaloacetic acid (manufactured by KANTO CHEMICAL CO., INC.), peroxidase (manufactured by TOYOBO CO., LTD.), and CHO-CE (cholesterol oxidase; manufactured by KIKKOMAN CORPORATION).

EXAMPLES

Example 1

The effect of an α-keto acid for stabilizing a cholesterol oxidase was evaluated by the following method.
(1) Specimen
Specimens A (specimens A0 to A3) and specimens B (specimens B0 to B3) comprising the following compositions were prepared.
<Specimens A (specimens A0 to A3)>

| | |
|---|---|
| MOPS (pH 7.0) | 20 mmol/L |
| CHO-CE | 2 kU/L |

α-Keto acid (see Table 1, no α-keto acid in specimen A0)
<Specimens B (specimens B0 to B3)>

| | |
|---|---|
| MOPS (pH 7.0) | 20 mmol/L |
| Triton X-100 | 1% |
| CHO-CE | 2 kU/L |

α-Keto acid (see Table 1, no α-keto acid in specimen B0)
(2) Reagent For Measuring Cholesterol Oxidase Activity
Reagent A and Reagent B comprising the following compositions were prepared.
<Reagent A>

| | |
|---|---|
| MOPS (pH 7.0) | 50 mmol/L |
| EMSE | 0.3 g/L |
| 4-AA | 0.1 g/L |
| BioAce | 0.3 g/L |
| PGM-50 | 10 g/L |
| Sodium cholate | 5 g/L |
| Peroxidase | 15 kU/L |

<Reagent B>
Solution of cholesterol in 2-propanol (5 mg/mL)
Reagent B (2 mL) was added to Reagent A (50 mL) and stirred well to thereby provide a reagent for measuring cholesterol oxidase activity.

(3) Difference in the Absorbances for a Specimen Immediately After Preparation

The specimen A1 immediately after preparation (2.4 μL) and the reagent for measuring cholesterol oxidase activity (225 μL) of (2) described above were added to a reaction cell. After warming at 37° C. for 5 minutes, the absorbance of the reaction solution, $E1_{A1(immediately\ after\ preparation)}$, was measured at a main wavelength of 546 nm and a sub-wavelength of 800 nm. The reaction solution was further warmed at 37° C. for 5 minutes, and the absorbance of the reaction solution 10 minutes after reaction, $E2_{A1(immediately\ after\ preparation)}$, was measured at a main wavelength of 546 nm and a sub-wavelength of 800 nm. $E1_{A1(immediately\ after\ preparation)}$ was subtracted from $E2_{A1(immediately\ after\ preparation)}$ to provide $\Delta E'_{A1(immediately\ after\ preparation)}$.

Similarly, the reaction was carried out using distilled water as a specimen. The absorbance of the reaction solution 5 minutes after reaction, $E1_0$, was subtracted from the absorbance of the reaction solution 10 minutes after reaction, $E2_0$, to provide $\Delta E_0$. $\Delta E_0$ was subtracted from $\Delta E'_{A1(immediately\ after\ preparation)}$ to provide the difference in the absorbances, $\Delta E_{A1(immediately\ after\ preparation)}$ for the specimen A1 immediately after preparation.

(4) Difference in the Absorbances for a Specimen After Preservation at 5° C. for 2 Weeks Except that the specimen A1 after preservation at 5° C. for 2 weeks was used instead of the specimen A1 immediately after preparation, the difference in the absorbances, $\Delta E_{A1(after\ preservation)}$ for the specimen A1 after preservation at 5° C. for 2 weeks was determined by the same method as in (3) described above.

(5) Residual Ratio of a Cholesterol Oxidase in the Specimen After Preservation at 5° C. for 2 Weeks The residual ratio of the cholesterol oxidase in the specimen after preservation at 5° C. for 2 weeks relative to the cholesterol oxidase in the specimen immediately after preparation was determined from $\Delta E_{A1(immediately\ after\ preparation)}$ determined in (3) described above and $\Delta E_{A1(after\ preservation)}$ determined in (4) described above, using the expression (II) described above. The results are shown in Table 1.

The residual ratio of the cholesterol oxidase in each of the specimens after preservation at 5° C. for 2 weeks relative to the cholesterol oxidase in each of the specimens immediately after preparation was determined by the same method as in (1) to (5) described above except that the specimens A2 and A3 and specimens B1 to B3 were each used as the specimen instead of the specimen A1. The results are shown in Table 1.

Furthermore, the residual ratio of the cholesterol oxidase in each of the specimens after preservation at 5° C. for 2 weeks relative to the cholesterol oxidase in each of the specimens immediately after preparation was determined by the same method as in (1) to (5) described above except that the specimen A0 or the specimen B0 was used instead of the specimen A1 and the expression (III) described above was used instead of the expression (II) described above. The results are shown in Table 1.

TABLE 1

| Specimen | α-Keto acid (Concentration) | Residual ratio (%) |
|---|---|---|
| A0 | — | 61 |
| A1 | Sodium pyruvate (0.5 g/L) | 88 |
| A2 | α-Ketoglutaric acid disodium (0.5 g/L) | 91 |

TABLE 1-continued

| Specimen | α-Keto acid (Concentration) | Residual ratio (%) |
|---|---|---|
| A3 | Oxaloacetic acid (0.5 g/L) | 80 |
| B0 | — | 71 |
| B1 | Sodium pyruvate (0.5 g/L) | 95 |
| B2 | α-Ketoglutaric acid disodium (0.5 g/L) | 85 |
| B3 | Oxaloacetic acid (0.5 g/L) | 79 |

As seen from Table 1, it was found that in case the specimens containing no surfactant (A0 to A3) were used or in case the specimens containing a surfactant (B0 to B3) were used, the residual ratio of the cholesterol oxidase in the coexistence of an α-keto acid was higher than that in the absence of an α-keto acid and was 75% or more. In contrast, in the absence of an α-keto acid or a salt thereof, the residual ratio was as low as less than 75%. Thus, it was found that allowing a cholesterol oxidase to coexist with an α-keto acid or a salt thereof in an aqueous medium stabilizes the cholesterol oxidase.

INDUSTRIAL APPLICABILITY

The present invention provides a method for stabilizing a cholesterol oxidase, a method for preserving a cholesterol oxidase, and a stabilized composition of cholesterol oxidase. The method for stabilizing a cholesterol oxidase, the method for preserving a cholesterol oxidase, and a stabilized composition of cholesterol oxidase according to the present invention are useful for clinical diagnosis such as metabolic syndrome.

The invention claimed is:

1. A method for stabilizing a cholesterol oxidase which comprises the steps of:
    preparing an aqueous solution of cholesterol oxidase;
    adding an α-keto acid or a salt thereof to the aqueous medium to prepare an aqueous solution comprising the α-keto acid or a salt thereof and the cholesterol oxidase; and
    preserving the aqueous solution comprising the α-keto acid or a salt thereof and the cholesterol oxidase at −5 to 45° C. for at least two weeks, wherein
    a concentration of the α-keto acid or a salt thereof in said aqueous solution is from 0.05 to 40 mmol/L, and
    the α-keto acid is selected from the group consisting of pyruvic acid, α-ketoglutaric acid and oxaloacetic acid.

2. The method for stabilizing a cholesterol oxidase according to claim 1, wherein said cholesterol oxidase is isolated.

* * * * *